United States Patent [19]

Russo et al.

[11] Patent Number: 5,080,225

[45] Date of Patent: Jan. 14, 1992

[54] UNIVERSAL DIAGNOSTIC SAMPLE PACKAGING TRAY AND POUCH

[76] Inventors: Laurence M. Russo, 1885-B Springer Rd., Mountain View, Calif. 94041; Joseph D. Russo, 3122 Bandera Dr., Palo Alto, Calif. 94304

[21] Appl. No.: 439,638

[22] Filed: Nov. 20, 1989

[51] Int. Cl.$^5$ ..................... B65D 85/30; B65D 81/26
[52] U.S. Cl. .................... 206/204; 206/443; 206/509; 206/564
[58] Field of Search ............ 206/204, 205, 363, 370, 206/438, 443, 446, 560, 564, 568-570, 509; 422/61, 104

[56] References Cited

U.S. PATENT DOCUMENTS

| | | | |
|---|---|---|---|
| 2,962,158 | 11/1960 | Struthers | 383/94 X |
| 2,987,174 | 6/1961 | Free et al. | 206/46 |
| 3,272,371 | 9/1966 | Weiner | 206/443 |
| 3,707,227 | 6/1972 | Britt | 206/443 |
| 3,746,161 | 7/1973 | Jones | 206/564 |
| 3,948,436 | 4/1976 | Bambara | 206/523 |
| 3,986,914 | 10/1976 | Howard | 383/63 X |
| 3,999,653 | 12/1976 | Haigh et al. | 383/102 |
| 4,213,528 | 7/1980 | Kreutz et al. | 206/204 |
| 4,224,416 | 9/1980 | Taylor et al. | 220/DIG. 30 |
| 4,240,547 | 12/1980 | Taylor | 206/204 |
| 4,267,928 | 5/1981 | Curry, Jr. | 206/583 |
| 4,282,984 | 8/1981 | Curry, Jr. | 220/404 |
| 4,361,226 | 11/1982 | Travis | 206/564 |
| 4,407,897 | 10/1983 | Farrell et al. | 206/204 |
| 4,495,082 | 1/1985 | Mita et al. | 252/194 |
| 4,501,360 | 2/1985 | Levy et al. | 206/446 |
| 4,572,361 | 2/1986 | Fontlladosa | 206/45.19 |
| 4,572,371 | 2/1986 | Asenbauer | 206/560 |
| 4,573,578 | 3/1986 | Greminger, Jr. et al. | 206/524.4 |
| 4,597,765 | 7/1986 | Klatt | 623/11 |
| 4,615,923 | 10/1986 | Marx | 428/35 |
| 4,619,361 | 10/1986 | Thomas, Jr. | 206/204 |
| 4,620,633 | 11/1986 | Lookholder | 206/523 |
| 4,637,061 | 1/1987 | Riese | 383/38 |
| 4,679,688 | 7/1987 | Soderholm et al. | 206/204 |
| 4,699,622 | 10/1987 | Toussant et al. | 604/389 |
| 4,706,996 | 11/1987 | Fasham | 282/1 |
| 4,735,308 | 4/1988 | Barner | 206/204 |
| 4,735,843 | 4/1988 | Noda | 428/137 |
| 4,736,850 | 4/1988 | Bowman et al. | 206/564 |
| 4,738,674 | 4/1988 | Todd et al. | 604/361 |
| 4,738,675 | 4/1988 | Buckley et al. | 604/379 |
| 4,740,528 | 4/1988 | Garvey et al. | 521/128 |
| 4,742,908 | 5/1988 | Thomas, Jr. et al. | 206/204 |
| 4,744,374 | 5/1988 | Deffeves et al. | 131/331 |
| 4,748,069 | 5/1988 | Cullen | 428/195 |
| 4,748,076 | 5/1988 | Saotome | 428/224 |
| 4,748,977 | 6/1988 | Guyot et al. | 128/156 |
| 4,753,643 | 6/1988 | Kassal | 604/359 |
| 4,753,834 | 6/1988 | Braun et al. | 428/74 |
| 4,755,405 | 7/1988 | Massucco et al. | 206/807 |
| 4,756,937 | 7/1988 | Mentzer | 428/2 |
| 4,756,937 | 7/1988 | Mentzer | 428/35 |
| 4,758,239 | 7/1988 | Yeo et al. | 604/366 |

(List continued on next page.)

FOREIGN PATENT DOCUMENTS

| | | | |
|---|---|---|---|
| 0922611 | 3/1973 | Canada | 206/568 |
| 1552810 | 9/1979 | United Kingdom | 206/204 |

Primary Examiner—Jimmy G. Foster
Attorney, Agent, or Firm—Jacques M. Dulin; Thomas C. Feix

[57] ABSTRACT

A diagnostic sample packaging tray and pouch for holding a variety of commonly used sample containers, such as tube, needle and slide combinations which are required for various testing procedures in medical practice. The tray is preferably constructed of a strong transparent thermoplastic material and is provided with at least one specially configured surface designed to securely hold the same containers. The tray can be a single-piece tray or a two-piece tray. The preferred embodiment is a single-piece tray which can be folded into a closed position so that a first portion of the tray folds over a second portion of the tray, whereby the two portions of the tray are locked into position, requiring a reasonable exertion of force to reopen the tray. The tray containing the used sample containers is placed within the pouch. The pouch includes a foldable flap having means for sealing closure of its open end. The pouch wall preferably comprises a three layer composite construction including a fluid permeable interior layer, an absorbent middle layer and a fluid impermeable exterior layer.

24 Claims, 8 Drawing Sheets

U.S. PATENT DOCUMENTS

| | | | |
|---|---|---|---|
| 4,784,267 | 11/1988 | Gessler et al. | 206/564 |
| 4,815,605 | 3/1989 | Brissier et al. | 206/523 |
| 4,826,003 | 5/1989 | Levy | 206/523 X |
| 4,861,632 | 8/1989 | Caggiano | 383/109 X |
| 4,890,936 | 1/1990 | Cooper | 383/109 |
| 4,903,827 | 2/1990 | Phelps et al. | 206/204 |
| 4,927,010 | 5/1990 | Kannankeril | 206/204 |
| 4,949,840 | 8/1990 | Brown | 206/204 |

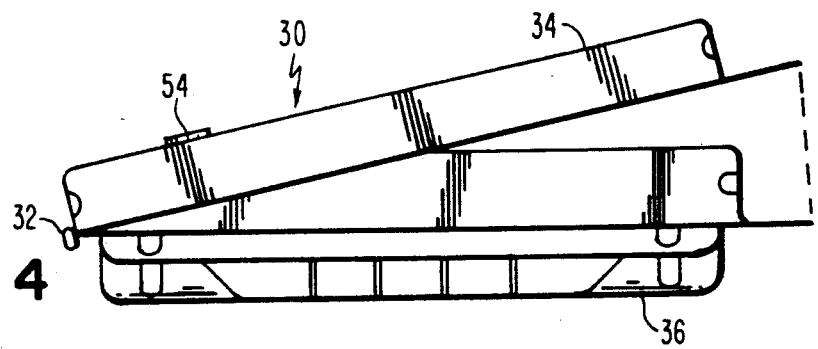
FIG. 4
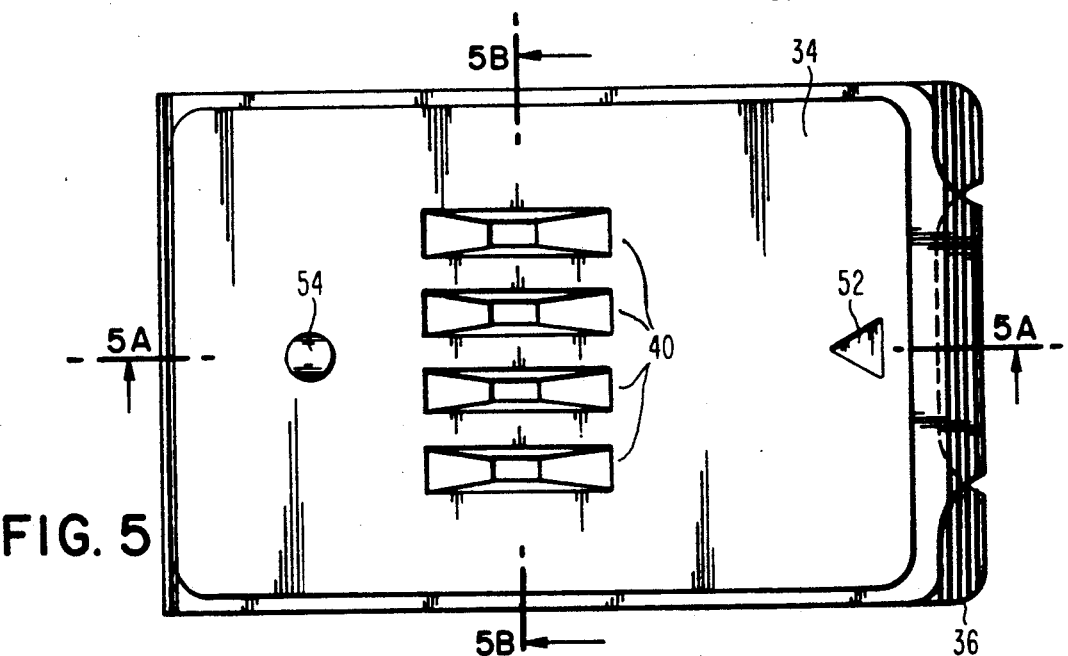
FIG. 5
FIG. 5A
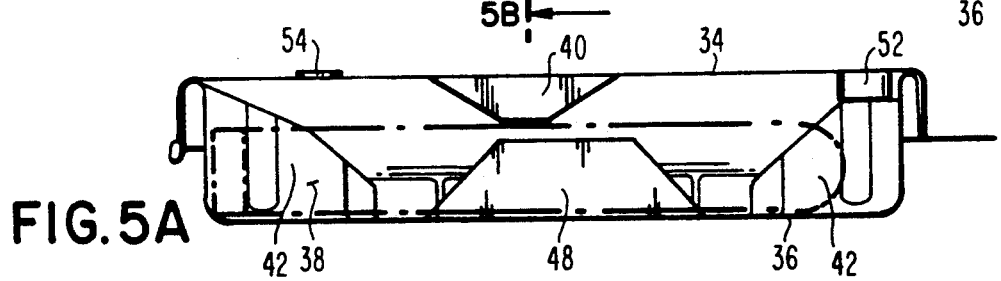
FIG. 5B
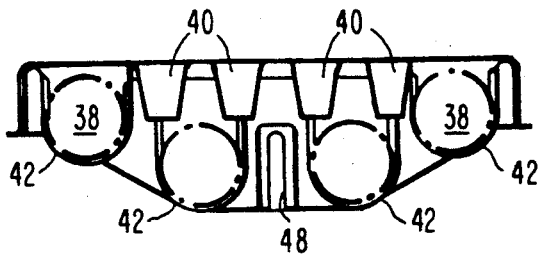

UNIVERSAL DIAGNOSTIC SAMPLE PACKAGING TRAY AND POUCH

CROSS REFERENCE TO RELATED APPLICATIONS

Applicants are inventors and owners of U.S. Ser. No. 257,725, filed Oct. 14, 1988, now U.S. Pat. No. 4,969,750 directed to a method of shipment and containment of a hazardous liquid. Applicants are also inventors and owners of Ser. No. 534,725 filed June 4, 1990, which is a continuation of Ser. No. 278,585 filed Dec. 1, 1988 and now abandoned, which Ser. No. 278,585 in turn is a continuation-in-part of parent Ser. No. 257,725. Ser. Nos. 534,725 and 278,585 are directed to packaging (pouches) for shipment and containment of hazardous liquids.

The [disclosures thereof are incorporated by reference herein and the] benefits of their filing dates are [for that disclosure] claimed.

BACKGROUND OF THE INVENTION

1. Field of the Invention

This invention pertains to packaging which can be used for handling, storage, and shipping of medical diagnostic samples. In particular, the invention relates to sample trays which have universal configurations, enabling them to hold a variety of shapes and sizes of sampling devices and vessels, and which trays are light weight and tough (exhibit good mechanical strength). The universal sample trays may be used individually, or may be placed within a pouch which is designed to reduce or eliminate the flow of any liquid from the tray into the surrounding environment. A universal tray inside a pouch makes an excellent shipping package for medical diagnostic samples.

2. Background of the Invention

Today's medical industry generates millions, if not billions, of samples taken for diagnostic purposes. Examples of such samples include urine, blood and tissue samples. These diagnostic samples are commonly drawn through needles and placed in tubes, or on slides (for example), for purposes of handling. Frequently the analysis of the diagnostic sample is not carried out at the clinic at which the sample was taken, but the sample is shipped to a laboratory which specializes in analysis of the particular kind of sample. Whether the sample is stored temporarily until analysis can be done at the clinic at which the sample was taken, or whether the sample is shipped to an outside laboratory for analysis, the sample must be stored, and in the latter case shipped, in a convenient manner.

Patent application Ser. No. 07/278,585 and its continuation Ser. No. 534,725 owned by the present applicants, and hereby incorporated by reference, discloses specialized packaging for shipment and containment of hazardous liquids, including medical diagnostic samples which may contain etiologic agents. This specialized packaging comprises a bag or pouch in which at least one container of liquid can be sealed so that the package completely surrounds and isolates the container of liquid. The bag or pouch comprises at least two layers, including an interior layer and an exterior layer. The interior layer of the bag or pouch is adjacent to the container and can be penetrated or permeated by liquid which escapes from the container, but the exterior layer of the pouch, which is in contact with the external ambient environment, is impermeable by the liquid or hazardous vapors thereof. One of the critical features of the bag or pouch is that it has a means for sealing the bag or pouch after the sample/container of liquid is placed inside, wherein the seal is impermeable by the liquid or vapors thereof. The pouch or bag can have numerous other features such as, for example, a layer capable of immobilizing liquid; a reactant present which deactivates or destroys an etiologic agent; and a liquid indicating means, whereby a visual indication that liquid is in direct contact with the pouch interior is automatically and continually provided at a location which can be observed from the exterior of the pouch.

It is known in the art to use styrofoam trays into which sample needles, tubes and slides are placed during sample kit assembly, for subsequent handling by medical personnel. The styrofoam tray can be placed in a shipping box, envelope or cylinder, to hold the samples in place within such container. However, in shipping samples such as tubes of blood, frequently the tubes break due to rough package handling, causing blood to leak out the edges of the styrofoam tray or cracks or breaks in the tray. Styrofoam trays are not known for their mechanical strength. Although a bag or pouch of the type described in patent application Ser. No. 07/278,585 can be used to prevent leakage of a liquid sample from the sample tray during shipment, and can help prevent breakage of the diagnostic sample container, there is a need for an improved sample tray which can be used during handling, storage and shipment of the diagnostic samples. Such a tray must be light weight, tough, and very importantly, inexpensive to manufacture. It is also preferred that the tray manufacturing process not be environmentally detrimental. For example, the blowing agents used to generate styrofoam are detrimental to the earth's ozone layer.

Some of the kinds of packaging presently known for shipment of hazardous liquids in general (but not particularly for the handling, shipping and storage of biological, diagnostic samples, as will be evident to one skilled in the art) are described below. Also described are diagnostic packaging systems presently known to the applicants in addition to the commonly used styrofoam trays described above.

U.S. Pat. No. 4,756,937 to Mentzer, issued July 12, 1988 describes a protective wrapping, barrier shield, receptacle, and/or liner in the packaging of a container or containers of hazardous chemical. These materials are demonstrated as layered structures, wherein at least one of the layers comprises a shock absorbing structure, and another of the layers is a porous structure which has been conditioned to react with the hazardous chemical. The multilayered structure can be formed into the configuration of a cup-like receptacle.

U.S. Pat. No. 4,573,578 to Greminger, Jr. et al., issued Mar. 4, 1986, discloses safety packages prepared for transportation of methanol, wherein ethyl cellulose having from about 45 to 46.5 weight percent substitution is employed as a sorbent. The drawings. at FIG. 1 show a multilayered bag comprising the sorbent, surrounding a jar or bottle which contains the methanol. The bag is tied at the top with a cord.

U.S. Pat. No. 4,706,996 to Fasham, issued Nov. 17, 1987, describes a hospital form set with detachable bag. This invention is concerned with a business form assembly for use in hospitals and capable of recording details of a medical test, for example, a blood test. The assembly comprises a forms sheet and a bag capable of receiving a container containing a test sample and having closure means at the mouth of the bag to secure the container in the bag. The bag is secured to the forms sheet by an adhesive. The drawings, at FIG. 3, show a single tube-shaped container inside a bag, with the bag secured to the forms set. The bag appears to be a clear or at least transparent plastic bag having rib and channel parts at one end which can be used to close the bag. The bag is not designed to protect the sample's tube-shaped container, as is evidenced not only by the drawings and general description of the assembly, but also by the fact that a drip tray is placed under the rack upon which the hospital form set with sample attached can be transported and stored. The system is designed especially to keep the data information form attached to a bag in which a single sample is placed, for handling within a hospital or clinic. This type of assembly is not useful in shipping samples to an outside testing/analysis lab, since each bag is designed to hold only one sample and provides no significant protection for the sample container.

U.S. Pat. No. 4,637,061 to Riese, issued Jan. 13, 1989, describes a specimen, sample collection and transport container. The specimen, sample collection and transport container comprises a flexible plastic bag which is separated into selectively sealed chambers by leakproof interlocking multiple track, reclosable fasteners. The bag comprises a sheet of coextruded polyethylene-Saran-polyethylene material which is folded in half and sealed at the side edges. An interior fastener substantially traverses the container parallel to the folded bottom, thereby defining a lower chamber. An entrance fastener is affixed to the upper edges to selectively seal the entrance. Gripper flaps are added to the exterior of the container to facilitate the opening of the interior fastener. The lower chamber is supplied with a fixative or transport solution which is introduced by clipping or puncturing the lower corner or edge of the bag. The corner or hole is then sealed.

U.S. Pat. No. 2,987,174 to A.H. Free et al, issued June 6, 1961, discloses a test sample container for collecting biological fluids such as urine, blood and the like for preservation during storage and transportation by mail and similar means to a laboratory where the specimens may be readily tested for the determination of the presence of various materials for diagnostic and therapeutic purposes. The claimed device is a device for collecting and transporting a urine sample, the device comprising a front sheet and a back sheet, each sheet having an inner and outer face and being joined along a common edge to form a folder which, in closed position, places the inner face of a front sheet in closely contiguous position with an inner face of a back sheet. A layer of moisture absorbent material is present on the inner face of both the front and back sheet. A section of bibulous urine sample absorbing material is affixed to one edge of the folder and is foldable into the opened folder between the non-wettable porous screens, out of direct contact with the layers of absorbent material. A deposit of urine preservative material is present on the bibulous material to stabilize the urine sample.

None of the sample containers or trays described above provides the functional, light-weight, tough sample tray of the kind needed by the medical industry today.

SUMMARY OF THE INVENTION

The diagnostic sample tray and pouch of the present invention is designed to hold a variety of commonly used sample containers, such as tube, needle and slide combinations which are required for various testing procedures in medical practice, thus making the tray and pouch "universal". The tray is designed to securely hold the sample container, for example, the tube, needle or slide, in place within the configuration of the tray. The tray can be a single-piece tray or a two-piece tray. The preferred tray embodiment is a single-piece tray, which is hinged so that the tray can be used in an open position or a closed position. In the closed position, a first portion of the tray is folded over a second portion of the tray, whereby the two portions of the tray are locked into position, requiring a reasonable exertion of force to reopen the tray. The tray can also be a two-piece design, wherein the two pieces lock together. However, a single-piece tray offers advantages in storage and inventorying. Thus, a preferred two-piece design is one wherein two single-piece trays are used in combination to double the number of samples which can be held within the combination tray.

Preferred embodiments of the universal diagnostic sample tray have a configuration which utilizes tray edge walls and tray cavities to form separation walls between samples and to act as brace holders of the samples. In addition, the preferred embodiments comprise a folded, rolled hinge design for the single-piece tray, so there are no sharp edges which are a hazard. In the most preferred single-piece tray design, the folded hinge extends outside the tray body so that none of the sample containers contact the hinge. Another feature of the preferred tray embodiments is a space provided near the ends of sample-tube holding cavities or forms, which space permits the use of a variety of different tube lengths and different sized tube stoppers.

It is also preferred that the material used to construct the universal sample tray be clear or transparent so that even when the tray is in a closed position, persons using the tray can see the kind and number of samples contained within the tray. Typically the tray will be constructed of a plastic material which offers both features of light-weight and good mechanical strength. The plastic preferred is thermoplastic which can be thermoformed, injection molded, compression molded, extruded, rotational molded, or processed using other commonly known techniques into the form of the tray.

Thermoforming of sheets of thermoplastic material into the tray is one of the more preferred fabrication methods, since thermoforming is one of the least expensive methods of forming the tray. Injection molding and extrusion can also be used to advantage in forming the tray. A lesser preferred but significant fabrication method is foaming of the thermoplastic material, using chemical blowing agents, under pressure into the desired configuration; or preparing foamed sheets of the thermoplastic material which are subsequently formed under pressure into the desired configuration.

Thermoplastic materials which can be used to fabricate the tray comprise, for example, polymers such as rigid or semi-rigid polyvinyl chloride (PVC), polycarbonate, acrylic, impact-modified acrylic, polystyrene, impact-modified polystyrene, acrylonitrile-polybutadiene styrene (ABS), polyethylene, polypropylene, and other similar polymers. Biodegradable formulations of such plastics are even more preferred. The most preferred of these materials are those which are clear or sufficiently transparent that the user can detect the kind and number of samples within the tray, as previously discussed. The foamed form of these thermoplastic materials can be used as previously discussed, however, typically the mechanical properties of the tray will not be as good and the tray will not be transparent. The advantage to foamed thermoplastic materials is the reduced material cost.

The most preferred sample tray is thermoformed from a sheet of thermoplastic which is heated to a sufficient temperature to permit the sheet to be drawn, or forced under pressure or vacuum, into the desired configuration. Typically the wall thickness of a thermoformed universal diagnostic sample tray can range from about 1 mil 0.001 inches) to about 300 mils, depending on the tray dimensions and the amount of draw in the tray design. The tray inside and outside dimensions can vary as required by the tray design. A typical example is a universal diagnostic sample tray which is formed from a sheet of thermoplastic about 15-25 mils thick. The formed tray will have lateral (lengthwise) dimensions up to about 13 inches, with a vertical height ranging from about 1 inch to about 3 inches, and a wall thickness ranging from about 1 mil up to the initial thickness of the thermoplastic sheet (15-25 mils), depending on the amount of localized draw demanded by the tray configuration. Increased wall thickness will permit an increase in the tray maximum lateral dimension, and in the amount of draw or deformation of the plastic sheet which can occur without the tray wall becoming unacceptably thin. One skilled in the art can, with minimal experimentation, determine the initial thermoplastic sheet thickness necessary to produce an acceptable range of wall thickness for a tray of specific dimensions. The acceptable wall thickness range is dictated by the particular application for which the tray will be used.

The tray containing the samples is then placed within a closeable pouch container. The pouch preferably comprises at least two layers, including an interior layer and an exterior layer, wherein the interior layer of the bag or pouch adjacent to the sample containers can be penetrated or permeated by any liquid, such as, for example, blood, which escapes from the sample containers, and wherein the exterior layer of the bag or pouch, the external portion of which is in contact with the ambient environment, is impermeable by the liquid and by any hazardous vapors therefrom.

At least one of the layers of the bag or pouch can be capable of immobilizing the liquid. When the immobilizing layer is other than the exterior layer, the exterior layer of the bag or pouch must be impermeable by at least the immobilized liquid and by any hazardous vapors therefrom.

At least one of the layers of the bag or pouch can be capable of destroying or deactivating the liquid to a chemical or physical composition which no longer poses a significant hazard to a person exposed to such deactivated composition.

At least one of the layers of the bag or pouch can be comprised of wicking channels which aid in distribution of the liquid to interior parts of the bag or pouch remote from the area of the container from which liquid is escaping.

At least a portion of at least one of the layers of the bag or pouch can comprise a liquid indicating means, whereby a visual indication that liquid is in direct contact with the interior of the bag or pouch is automatically and continually provided at a location which can be observed from the exterior of the bag or pouch.

BRIEF DESCRIPTION OF THE DRAWINGS

FIG. 1 shows a side view of the universal sample tray, and particularly the feature wherein the first part of the tray folds over the second part of the tray to place the tray in a closed position.

FIGS. 2, 2A, and 2B show the universal sample tray in a closed position. View 2A shows the hinge feature of the tray more clearly, and shows a sample tube held in a cavity position within the tray. FIG. 2B shows how cavities or forms in the top of the tray work in combination with the cavities or forms in the bottom of the tray to hold the samples very securely in place.

FIG. 3 shows the universal sample tray in the open position. The cavities and other forms within the tray which act to hold the samples in place and to provide mechanical strength to the tray are clearly shown, as are the ridges in the levers on the first and second parts of the tray to which pressure is applied to open the tray from a closed position.

FIGS. 4-6 show another preferred embodiment of the universal sample tray which is very similar to embodiment shown in FIGS. 1-3. However, the cavities and forms of this second preferred embodiment are slightly different, and are provided to show that there are several manners in which the same function can be provided, since it is contemplated that one skilled in the art could make such modifications and still fall within the scope of the present invention.

FIG. 7 shows a different hinge construction and different rigidizing structures along the edges of the tray. FIG. 9 shows this preferred embodiment of the universal sample tray in an open position, with needle and tube samples shadowed in to indicate the manner in which the cavities and forms within the tray hold such samples.

DETAILED DESCRIPTION OF THE PREFERRED EMBODIMENTS

The present invention comprises a universal sample tray which can be used for handling, storage and shipment of medical diagnostic samples. The tray can be used individually, or can be used in combination with a bag or pouch which provides additional protection for samples stored or shipped within the tray.

Figure 1:
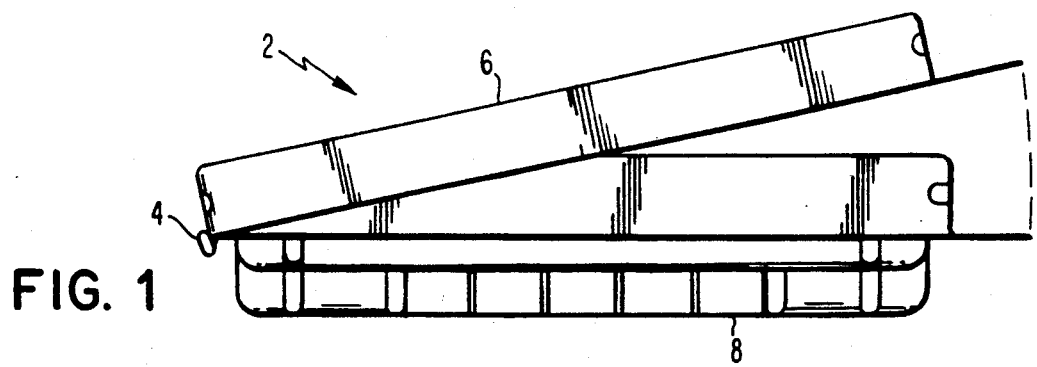
FIGS. 1-3 show one of the preferred embodiments of the universal sample tray of the present invention.
Figure 2:
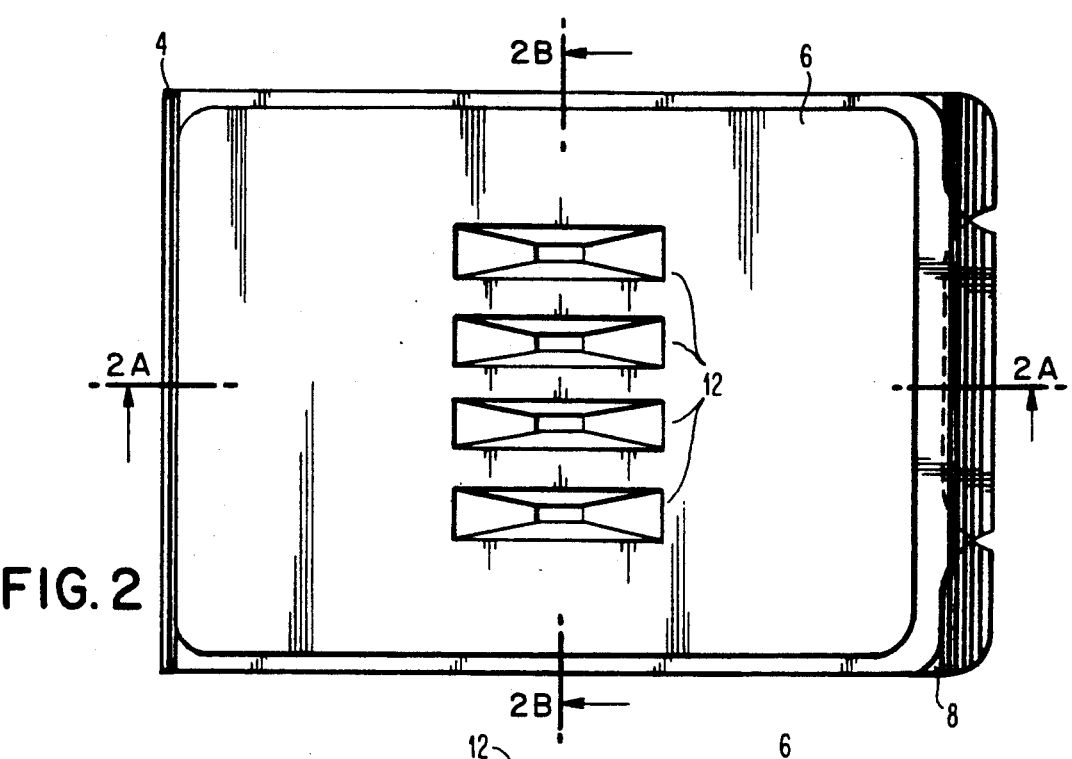
Figure 2A:
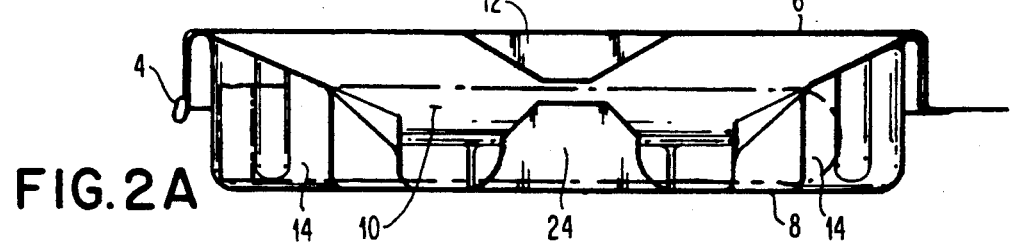
Figure 2B:
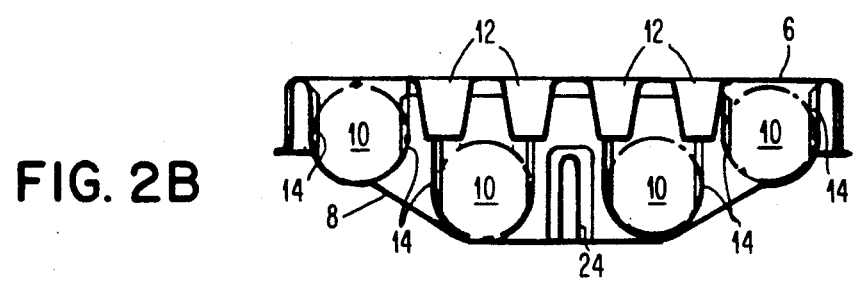

The universal sample tray is designed to hold a variety of tubes, needles and slides which are commonly used in medical practice. Referring to FIGS. 1-4, which show one preferred embodiment of the universal sample tray, FIG. 1 shows a single-piece tray 2 which is hinged 4 so it can be used in an open or closed position. A first portion 6 of tray 2 can be folded over a second portion 8 of tray 2 to place tray 2 in a closed position. The top view of closed tray 2 is shown in FIG. 2. Sections of FIG. 2, show a better view of how first portion 6 of tray 2 acts in combination with second portion 8 of tray 2 to more securely hold the samples in position within tray 2. FIG. 2A, shows, in shadow, a sample tube 10 held in place by forms 12 extending downward from first part 6 of tray 2 and forms 14 extending upward from second portion 8 of tray 2. Forms (or cavities) 12 extending downward from first portion 6 of tray 2 can also be used to hold sample containers, such as needles. Preferably, forms 12 are designed to hold tubes or needles at their center, enabling forms 12 to hold tubes or needles of varying length.

Figure 3:
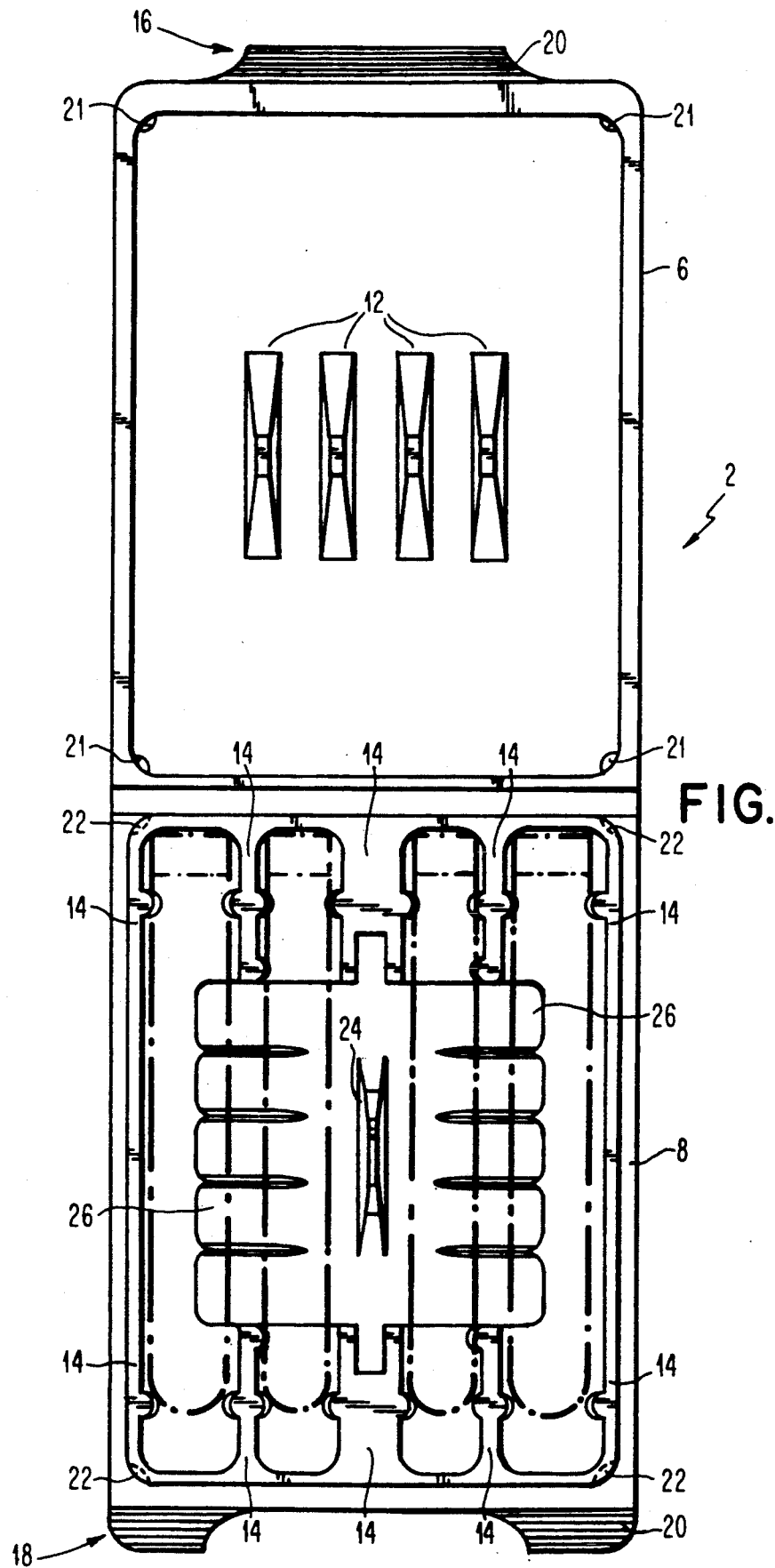

FIG. 3 shows universal sample tray 2 in its open position. FIG. 3 provides a good view of opening and closing levers 16 and 18 which make up a part of first portion 6 of tray 2 and second portion 8 of tray 2, respectively. These levers can have grooves 20 in them if desired to assist in the opening and closing process. Tray first-locking configurations 21 at the outer edges of first portion 6 of tray 2 fit into second-locking configurations 22 at the outer edges of second portion 8 of tray two to provide a mechanism for holding the tray in a closed position until sufficient force is applied to opening and closing levers 16 and 18 to cause the tray to open. FIG. 3 also shows another sample positioning form 24 in second portion 8 of tray 2. Sample positioning form 24 can be used to hold various sized tubes or needles in place within the space between the two centermost forms 12 of first portion 6, when tray 2 is in a closed position. In addition, by extending a section 26 of second portion 8 further away from the inner surface of second portion 8 (which mates with the inner surface of first portion 6), stiffening, bracing, and ease of access to samples placed within second portion 8 of tray 2 is provided, adding to the overall mechanical strength and dimensional stability of the tray as well as to ease of use.

The thermoformed universal sample tray of the kind shown in FIGS. 1-3 was approximately 5-7 inches in length in the closed position, approximately 3-4 inches in width, and had a cross-sectional vertical height ranging from about 1.25 to about 3 inches, depending on the tray cross-sectional location. The wall thickness of the thermoformed semirigid PVC ranged from about 2 mils to about 20 mils, depending on the depth of draw at a particular configuration location.

Figure 6:
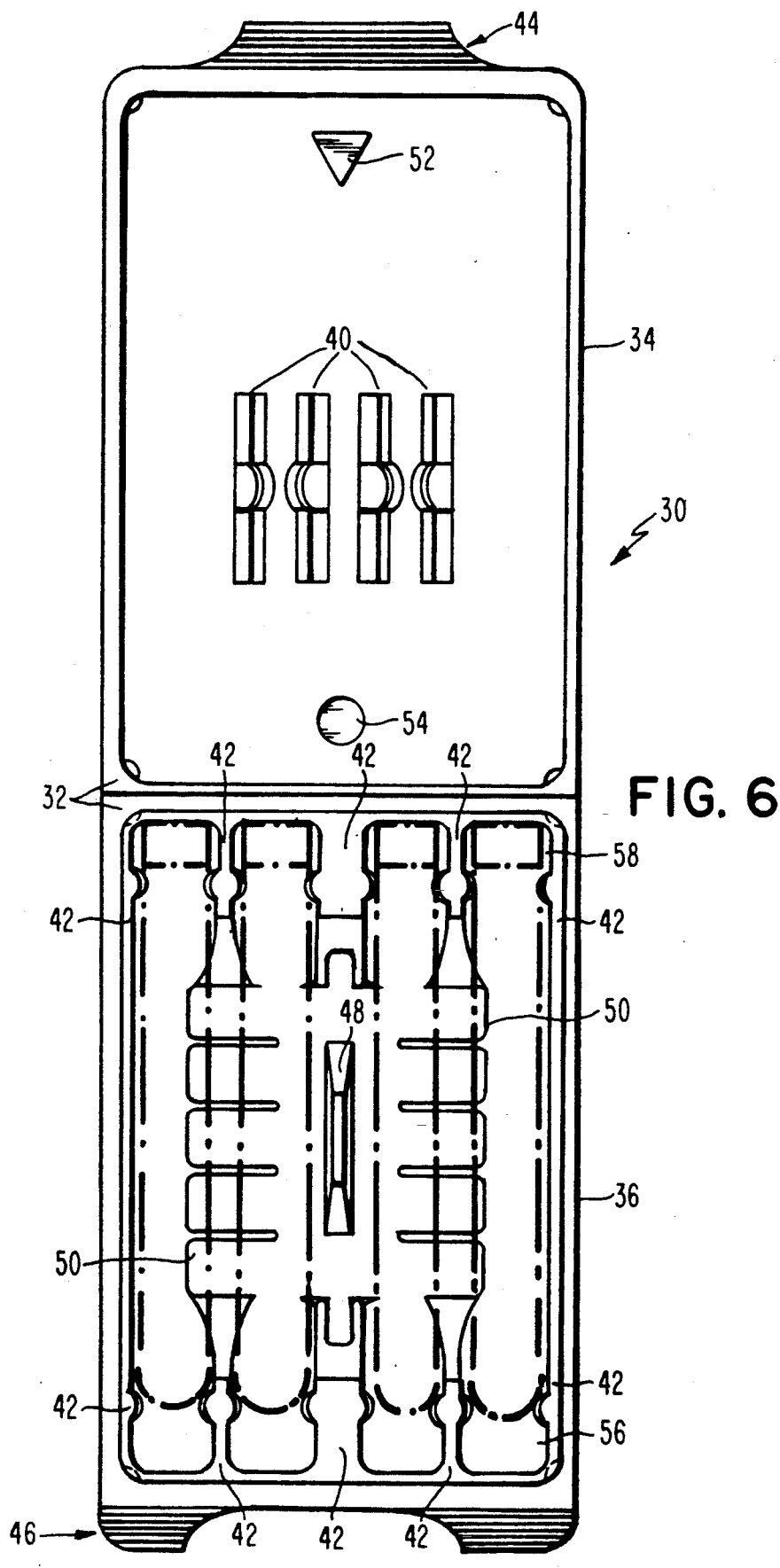

Referring to FIGS. 4-6, which show another preferred embodiment of the universal sample tray, FIG. 4 shows a single-piece tray 30 which is hinged 32 via a flat section in the center of the tray which folds to make hinge 32. A first portion 34 of tray 30 can be folded over a second portion 36 of the tray to place the tray in a closed position. The top view of closed tray 30 is shown in FIG. 5. Sections of FIG. 5 show a better view of how first portion 34 of tray 30 acts in combination with second portion 36 to more securely hold samples in position within tray 30. FIG. 5A shows, in shadow, a sample tube 38 held in place by forms 40 extending downward from first portion 34 and forms 42 extending upward from second portion 36 of tray 30. Forms or cavities 40 are also used to hold sample containers such as needle size structures. Preferably, forms 40 are designed to hold tubes or needles at their center, thus permitting the use of forms 40 with tubes or needles of various length.

FIG. 6 shows universal sample tray 30 in its open position. FIG. 6 provides a good view of opening and closing levers 44 and 46 which make up a part of tray 30 first portion 34 and second portion 36, respectively. FIG. 6 shows an additional sample positioning form 48 in second portion 36 of tray 30. Sample positioning form 48 is designed to hold tubes or needles in place within the space between the two centermost forms 40 of first portion 34 when tray 30 is in a closed position. In addition, by extending a section 50 of second portion 36 further away from the inner surface of second portion 36 (which mates with the inner surface of first portion 34 of tray 30), stiffening, bracing, and ease of access to samples placed within second portion 36 of tray 30 is provided, adding to the overall mechanical strength and dimensional stability, as well as ease of use of tray 30.

Formation 52 protrudes into the interior of first portion 34 while formation 54 protrudes out from the exterior of first portion 34 of tray 30. Formations 52 and 54 provide an interlocking mechanism which permits two trays to be stacked together.

It is also possible to use two single-piece trays together to form one larger tray with twice the sample capability. To do this, one opened tray 30, hereinafter described as the first tray 30, is placed atop another open tray 30, hereinafter described as the second tray 30, so that the first tray 30 and second tray 30 cavities are face to face, doubling the open interior size available from that of a single tray. The ends of the trays are reversed so that lever 44 of the first tray 30 is in contact with lever 46 of the second tray 30. This permits forms 40 extending downward from the first tray 30 to work in combination with forms 42 extending upward from the second tray 30, and forms 42 which now extend downward from the first tray 30 to work in combination with forms 40 which now extend upward from second tray 30.

Spaces 56 and 58 which are near the opening and closing lever 46 and near hinge 32 in second portion 36 of tray 30, respectively, provide room to accomodate various sizes of tubes and tube caps or stoppers.

The thermoformed universal sample tray of the kind shown in FIGS. 4–6 was approximately 5–6 inches in length in the closed position, approximately 3–4 inches in width, and had a cross-sectional vertical height ranging from about 1–3 inches, depending on the tray cross-sectional location. The wall thickness of the thermoformed semi-rigid PVC ranged from about 2 mils to about 20 mils, depending on the depth of draw at a particualr configuration location.

Figure 7:
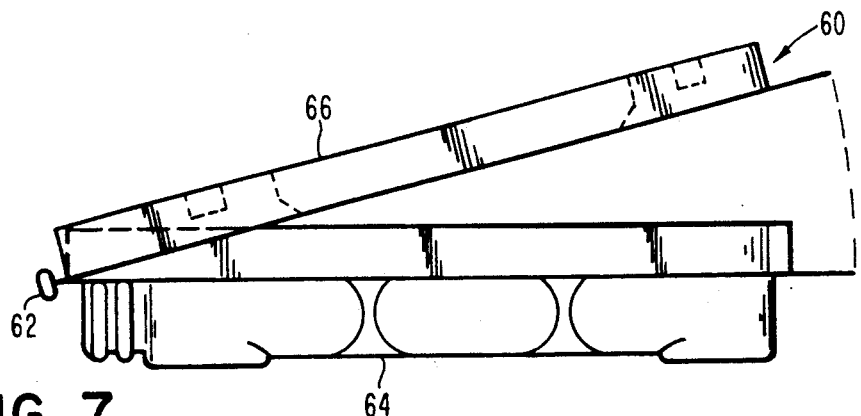
FIGS. 7-9 show another preferred embodiment of the universal sample tray wherein the hinge design and the cavities and forms within the tray show even a greater difference while performing essentially the same function as the embodiment shown in FIGS. 1-3.
Figure 8:
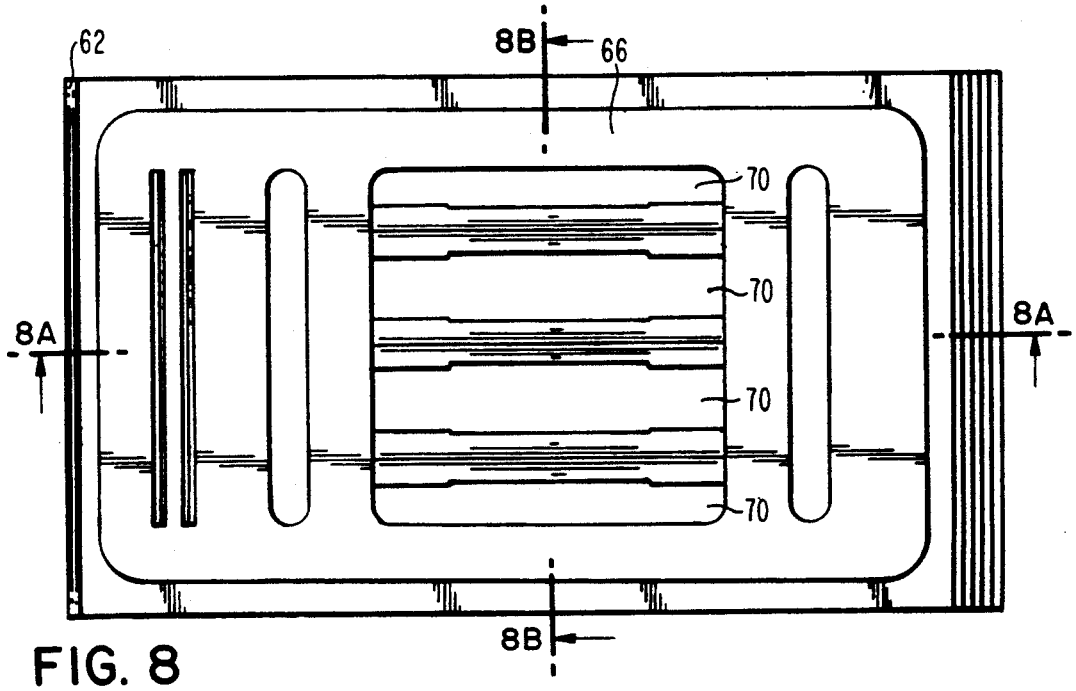
Figure 8A:
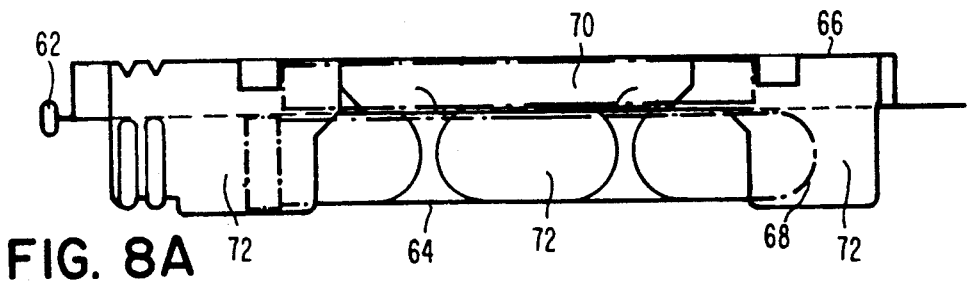
FIGS. 8A and 8B show a different sample holding configuration both in the top and bottom of the tray.
Figure 8B:
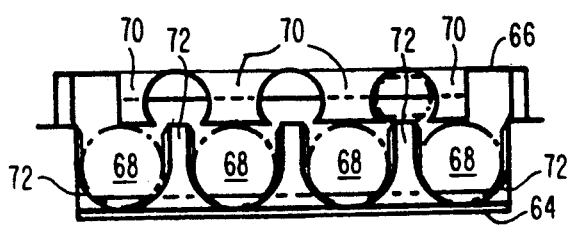

Referring to FIGS. 7–8, which show yet another preferred embodiment of the universal sample tray, FIG. 7 shows a single-piece tray 60 which is hinged 62 via a flat section in tray 60 which folds to form hinge 62 behind second portion 64 of tray 60. A first portion 66 of tray 60 is folded over second portion 64 to close tray 60 and form hinge 62. The top view of closed tray 60 is shown in FIG. 8. Sections of FIG. 8 show a better view of how first portion 66 of tray 60 acts in combination with second portion 64 to more securely hold samples in position within closed tray 60. FIG. 8A shows, in shadow, a sample tube 68 held in place by forms 70 extending downward from first portion 66 and forms 72 extending upward from second portion 64 of tray 60. Forms or cavities 70 are also used to hold sample containers such as needle size structures.

Figure 9:
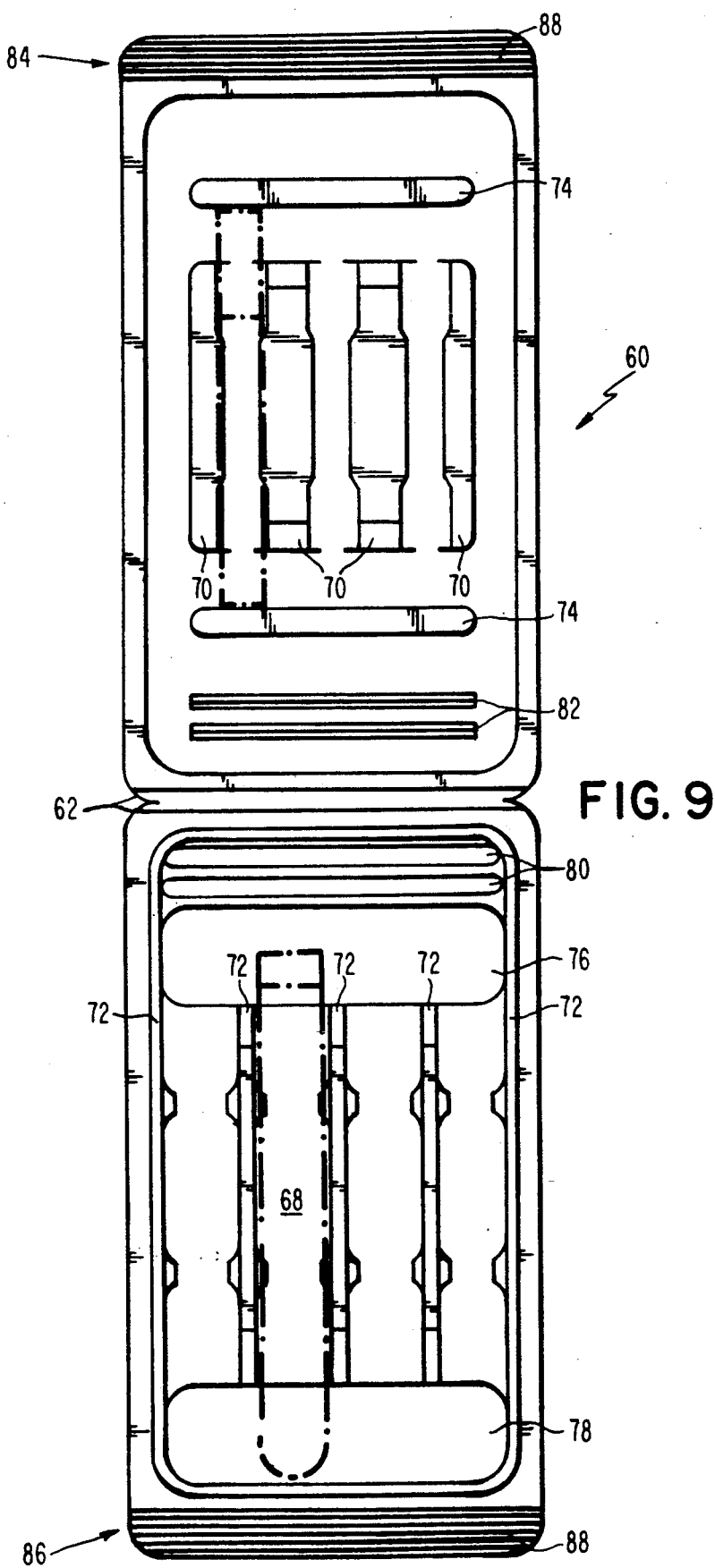

FIG. 9 shows universal sample tray 60 in its open position. FIG. 9 shows barrier formations 74 which provide bracing and support for samples held in position by forms 70, while simultaneously increasing the structural stability of tray 60. Spaces 76 and 78 located near hinge 62 and the opening edge, respectively, of tray 60 permit the use of tube lengths and tube caps or stoppers of various sizes. Concave (or depression) formations 80 provide a location for slide sample insertion, while simultaneously increasing the structural stability of tray 60. Barrier formations 82 work in combination with formations 80 to hold the slide samples in place. Opening and closing levers 84 and 86 can have grooves 88 in them to assist in the opening and closing operation.

The thermoformed universal sample tray of the kink shown in FIGS. 7–9 was approximately 6–8 inches in length in the closed position, approximately 3–4 inches in width, and had a cross-sectional vertical height ranging from about 1–2 inches, depending on the tray cross-sectional location. The wall thickness of the thermoformed semi-rigid PVC ranged from about 1 mil to about 20 mils, depending on the depth of draw at a particular configuration location.

Figure 10:
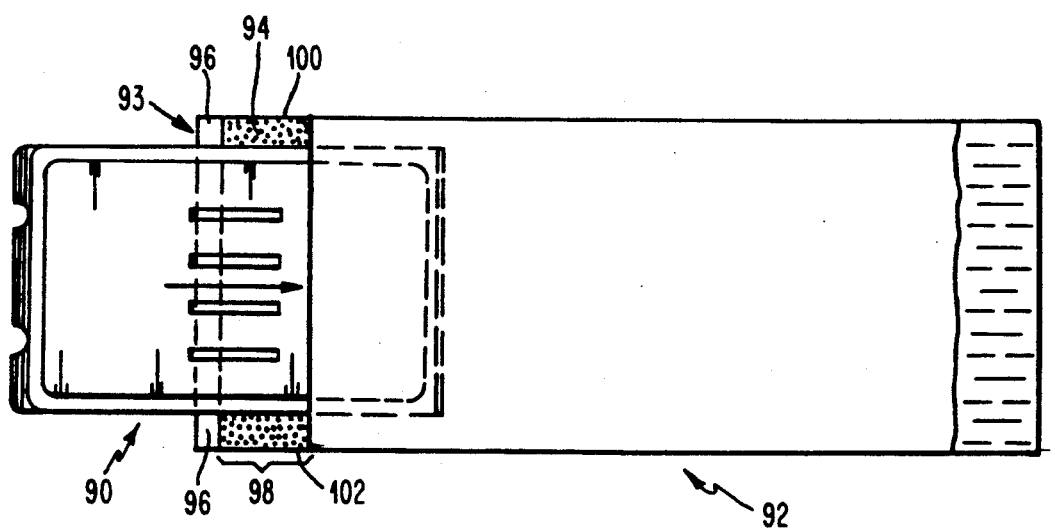
FIGS. 10-11 show one embodiment of the invention wherein the universal sample tray is placed within a storage or shipping pouch having an end closure. The closure can be of the type which provides an impermeable seal, or of the type which merely closes but does not seal.
Figure 11:
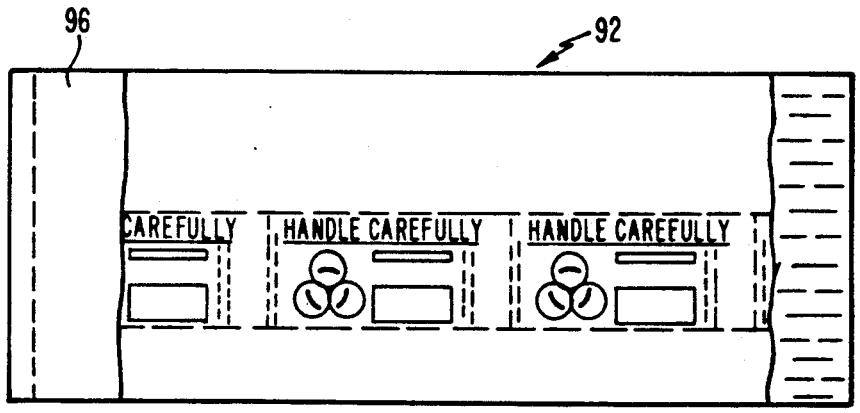

FIG. 10 shows one embodiment of the invention wherein a universal sample tray 90 is inserted into a storage or shipping pouch 92 having an end-type opening 93. Pouch 92 can be closed or sealed at end-type opening 93, using, for example, a layer of adhesive 94 applied to the inside surface of opening edge 96 of pouch 92. If the a sufficient width 98 of adhesive 94 is used, at least along side edges 100 and 102, so that upon folding edge 96 over to close pouch 92 the adhesive seals the entire length of side edges 100 and 102, pouch 92 can be made to have an impermeable seal, depending on the adhesive used. The invention contemplates the use of pouches which are closed but not sealed, and the use of pouches which are impermeably sealed. In addition, numerous other methods of closing or sealing pouch 92 can be used, such as "zip top" closures (comprising various bar and channel formations), and heat sealing. FIG. 11 shows a back view of the pouch of FIG. 10.

Figure 12:
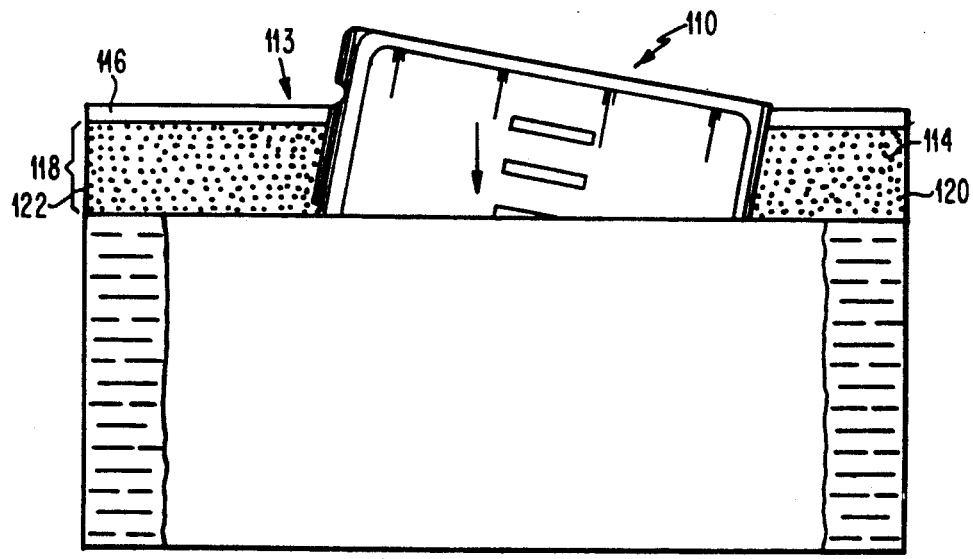
FIG. 12 shows another embodiment of the invention wherein the sample tray is placed within a storage or shipping pouch having a side closure. The pouch closure can provide an impermeable seal if desired.

FIG. 12 shows another embodiment of the invention wherein a universal sample tray 110 is inserted into a storage or shipping pouch 112 having a side-type opening 113. Pouch 112 can be closed or sealed at side-type opening 113 using, for example, a layer of adhesive 114 applied to the inside surface of opening edge 116 of pouch 112. If a sufficient width 118 of adhesive 114 is used, at least along side edges 120 and 122, so that upon folding edge 116 over to close pouch 112 the adhesive seals the entire length of side edges 120 and 122, pouch 112 can be made to have an impermeable seal, depending on the adhesive used. Again, the invention contemplates the use of pouches which are closed but not sealed as well as pouches which are impermeably sealed.

FIGS. 13A –18 show additional embodiments for the pouch wherein each pouch disclosed is constructed of a three layer composite comprising an interior permeable layer, an adjacent layer of absorbent or adsorbent material, and an exterior impermeable layer also adjacent to the absorbent or adsorbent material.

Figure 13A:
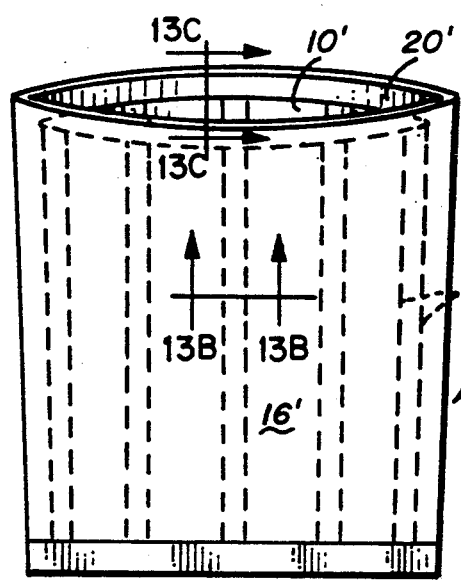
FIG. 13A shows a pouch having wicking channels built in to assist in transporting liquid which has escaped form the container to pouch areas remote from the container location from which the liquid has escaped.
Figure 13B:
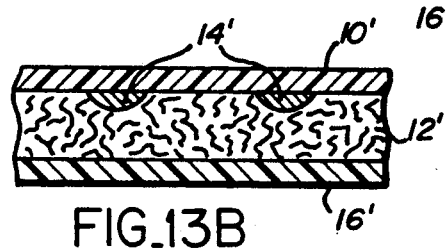
FIG. 13B shows a cross section of the pouch of 13A, the pouch having a permeable layer for an interior surface, with an absorbent material adjacent to the permeable layer, and wherein the absorbent material has been compressed into wicking channels, and having an impermeable exterior layer which is also adjacent to the absorbent material.
Figure 13C:
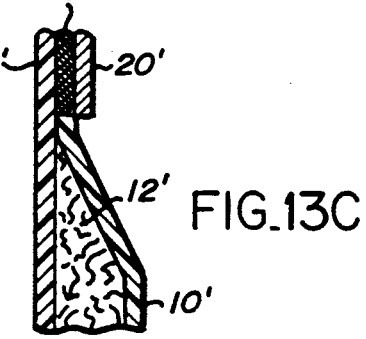
FIG. 13C shows a cross section of the upper, sealable edge of the pouch. The sealable edge comprises the exterior impermeable layer, with a layer of sealant applied to the interior surface of the impermeable layer, and having a release tape applied over the sealant surface, the release tape to be removed prior to sealing the pouch.

Referring to FIGS. 13A–13C, FIG. 13A shows the overall structure of the pouch prior to placement of a hazardous liquid container inside. The pouch 1″ has wicking channels built in to assist in transporting liquid which has escaped from the container to pouch areas remote from the container location from which the liquid has escaped. FIG. 13B shows a cross section of the packaging material composite, wherein as interior permeable layer 10′ is adhered to or placed proximate to an absorbent material 12′ which comprises depressions 14′ which function as wicking channels for distribution of liquid which has permeated layer 10′. An impermeable exterior layer 16′ is adhered to or placed proximate to absorbent material 12′. The pouch shown in FIGS. 13A and 13B could also have been fabricated without the wicking channels so long as the absorbent material 12′ can transfer the liquid adequately. FIG. 13C shows a cross section of the upper, sealable edge of the pouch. The sealable edge comprises the exterior impermeable layer 16′ with a layer 18′ applied to the interior surface of impermeable layer 16′. A release tape 20′ faces (covers) sealant layer 18′ until such time as the bag is to be sealed; at that time release tape 20′ is removed and the open edges of the bag comprising sealant 18' are brought together to seal the bag. Exterior impermeable layer 16' may be bonded to permeable layer 10' at a point below sealant layer 18', as shown in FIG. 13C. Depending on the materials used for impermeable layer 16' and permeable layer 10', the bonding may be accomplished by heat sealing or by application of a sealant or adhesive between the two layers. (A sealant or adhesive between layers 16' and 10' is not shown in FIG. 13C).

Figure 14:
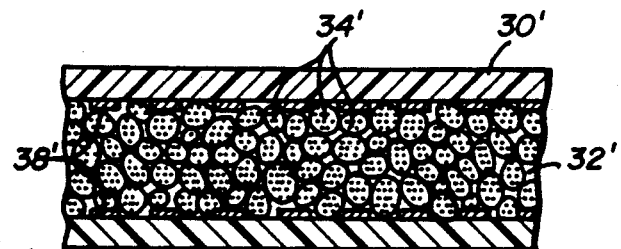
FIG. 14 shows a cross section of a packaging material having an absorbent or adsorbent material which includes a reactant capable of destroying or deactivating the hazardous liquid. The interior, permeable layer and exterior impermeable layer of the packaging material are bonded to the absorbent/adsorbent material using a dot matrix adhesive.

Referring to FIG. 14, a permeable interior layer 30' is adhered or placed proximate to an absorbent 32', which includes a reactant 34' capable of destroying or deactivating the hazardous liquid. An impermeable exterior layer 36' is adhered to or placed proximate to the exposed side of the layer of absorbent 32'. In FIG. 14, a dot matrix adhesive 38' is shown bonding permeable interior layer 30' and impermeable layer 36' to absorbent 32'.

Figure 15:
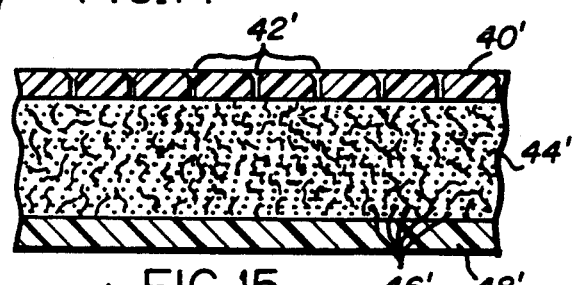
FIG. 15 shows a cross section of packaging material which comprises a perforated permeable interior layer bonded into intimate contact with a fibrous absorbent which is bonded to a vapor impermeable exterior layer. The fibrous absorbent contains a coagulant or thickening agent.

Referring to FIG. 15, a permeable interior layer 40' comprising perforations 42' is adhered to at least a portion of the fibers making up a first surface of absorbent 44'. An exterior impermeable layer 48' is adhered to at least a portion of the fibers making up the second surface of absorbent layer 44'. Absorbent layer 44' also comprises a coagulant 46' which further assists in immobilizing the hazardous liquid within absorbent layer 44'.

Figure 16:
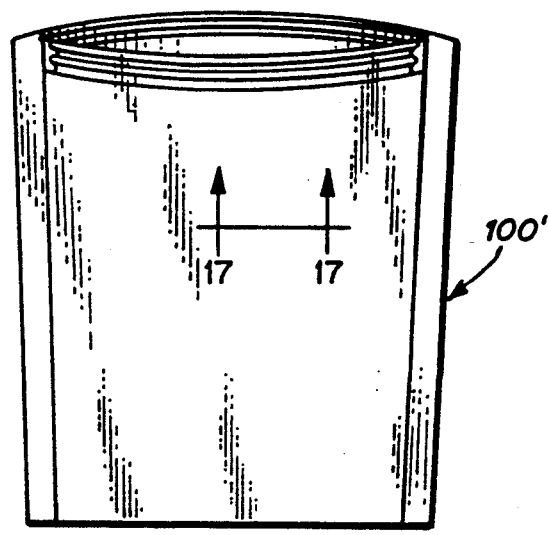
FIG. 16 shows a pouch having a folded bottom and heat-sealed sides, and having an interlocking fastener as the means of closure or sealing of the pouch.
Figure 17:
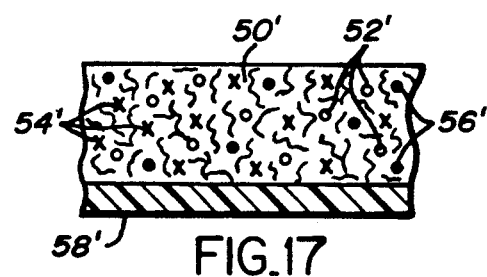
FIG. 17 shows a cross section of composite material which comprises the pouch shown in FIG. 16. The composite material comprises an interior layer of cellulosic wadding. The wadding contains a coagulant, a biocide, and an absorbent. The wadding layer is adjacent to an exterior impermeable layer comprised of a plastic.
Figure 18:
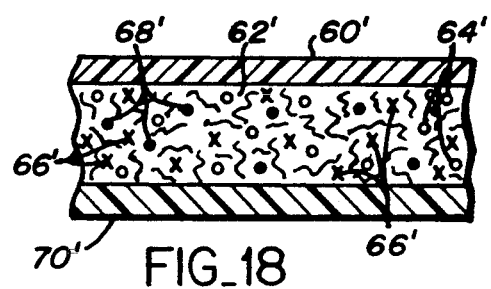
FIG. 18 shows a second, different composite material cross section which can comprise the pouch shown in FIG. 16. The composite material comprises an interior permeable layer having as an adjacent layer a first side of a layer of cellulosic wadding. The wadding contains a coagulant, a biocide, and an absorbent. The second side of the layer of cellulosic wadding is adjacent to an exterior impermeable layer. The exterior impermeable layer typically comprises a plastic such as polyethylene or polypropylene.

Referring to FIGS. 16 and 17, FIG. 16 shows the overall structure of a pouch 100' comprising a preferred embodiment of the present invention, prior to placement of a liquid container inside. FIG. 17 shows a cross sectional schematic of the pouch material composite, wherein an internal layer of cellulosic wadding 50' which contains a blood coagulant 52', a biocide 54', and an absorbent 56', is adhered to an exterior layer 58' which comprises an impermeable plastic. An alternate cross sectional schematic for the material composite which can be used to fabricate the pouch shown in FIG. 17 is shown in FIG. 18. FIG. 18 shows an interior permeable layer 60' adhered to or placed proximate to a layer of cellulosic wadding 62' which contains a blood coagulant 64', a biocide 66', and an absorbent 68', wherein the wadding 62' is adhered on its other surface to an exterior layer 70' which comprises an impermeable plastic. The most preferred embodiment of the material composite shown in FIGS. 17 and 18 uses a polyacrylate absorbent and a polyethylene exterior layer.

Examples of preferred absorbents include fibrous, cotton-like materials of the type described in U.S. Pat. No. 4,495,082 to Mita et al., which is hereby incorporated by reference; cellulosic wadding; paper wadding; superwicking crosslinked polyurethane foam compositions of the type described in U.S. Pat. No. 4,740,528 to Garvey et al., which is hereby incorporated by reference; crystalline, microporous siliceous materials of the kind described in U.S. Pat. No. 4,744,374 to Deffeyes et al., which is hereby incorporated by reference; sodium/calcium borosilicate glass microspheres and fibers in general, and particularly mineral fibers of the type described in U.S. Pat. No. 4,748,977 to Guyot et al., which is hereby incorporated by reference; cellulosic material, particularly fibrous products impregnated with a water absorbent acrylic polymer, of the type described in U.S. Pat. No. 4,748,076 to Satomef monofilaments of fibers of a thermoplastic material, and in particular those having a bilobalshaped cross sections of the type described in U.S. Pat. No. 4,754,834 to Braun et al., which is hereby incorporated by reference; vermiculite; dry colloidal silica, and similar absorbent materials. One skilled in the art can select an absorbent which is compatible with the liquid to be absorbed.

Typically, for shipment of blood samples, glass tubes of blood are placed in one of the tray embodiments of FIGS. 1-9, and the tray containing the tubes is placed inside one of the pouch embodiments of FIGS. 10-18. For shipment of such a tray full of samples, the preferred package comprises at least an interior layer of cellulosic wadding having a density ranging from about 0.3 to about 0.5 grams per square inch, used in combination with a polyethylene film ranging in thickness from about 0.5 to about 1.5 millimeters. For a heavier industrial application, the layer of cellulosic wadding should range from about 0.5 to about 1.0 grams per square inch, used in combination with a polyethylene film ranging in thickness from about 0.5 to about 2.5 millimeters.

One skilled in the art can calculate the cost of fabricating various packaging material composite structures and determine the combination of materials and relative thicknesses which should provide a cost advantage in manufacture of the packaging. Minimal experimentation combined with cost calculations will enable formulation of a preferred composite structure for a given application.

While the above described embodiments for the pouch disclose the use of an absorbent in a portion or layer of the packaging material, it is understood that the pouch may also contain other packaging materials capable of immobilizing liquids including but not limited to adsorbents, coagulants, gel-forming agents, or operative combinations thereof. Use of a coagulant or gel-forming agent or a deactivating agent such as a biocide will also depend on the application.

Numerous different methods of closing or sealing the bag or pouch can be used. Preferred closing or sealing methods, such as the strip/layer of adhesive previously described, provide a tamper-evident means for determining whether the diagnostic samples have remained undisturbed in terms of their contents since the closing of the bag or pouch.

There are numerous possible variations in the package structure and composition which can be used to practice the method of the present invention. It is intended that the scope of the present invention not be limited to the specific examples presented herein, but that those variations and modifications which come within the true spirit and scope of the present invention as presented in the appended claims be included.

What is claimed is:

1. A universal diagnostic specimen sample tray for shipping in commerce primary containers having etiologic material-containing diagnostic specimens, comprising a secondary container having in operative combination:
   a) a first lid portion and a second base portion;
   i) said first lid portion having an exterior upper surface and peripheral sidewalls depending therefrom;
   ii) said second base portion having upstanding peripheral sidewalls and an exterior bottom surface spanning said sidewalls;
   iii) said bottom surface of said base being spaced from said upper surface of said lid and said lid sidewalls are interlockingly engageable with said sidewalls of said base;
   b) both said lid and said base portions include a plurality of spaced interior ribs defining a plurality of individual recesses for retainingly engaging a variety of shapes and sizes of primary containers, sampling devices or specimen slides for said etiologic agent-containing diagnostic samples;

c) said sample tray comprising thin rigid, but flexible and resilient, transparent plastic so that the nature and condition of substantially all of the primary containers can be viewed from the exterior for survey of whether the sample has a hazardous nature and whether the container is open or broken;

d) said recesses including means for snap-fittingly retaining generally tubular primary containers medial of their ends;

e) said walls including exterior peripheral sidewalls defining an interior volume between said walls and said surface in both said lid portion and said base portion;

f) said surfaces including a plurality of ribs spaced inwardly from said exterior peripheral walls and formed as recesses from said exterior upper and bottom surfaces;

g) said ribs extending short of said peripheral walls to provide additional space for closure members for at least some of said primary containers; and h) at least some of said ribs of said lid being offset with respect to ribs of said base so that said lid ribs oppose and define said container spaces in said base, and assist in retaining in place at least one of said primary containers when receivingly engaged in said base recesses, and at least some of said ribs in said base oppose and define said container spaces in said lid, and assist in retaining in place at least some of said primary containers when receivingly engaged in said lid recesses.

2. A universal diagnostic specimen sample tray as in claim 1 wherein:

a) said lid and said base portions include a common hinge member along one common edge to form a one-piece tray assembly in which said lid sidewalls matingly engage said base sidewalls in the closed position.

3. A universal diagnostic specimen sample tray as in claim 2 wherein:

a) each of said lid and said base include at least one plastic flange extending outwardly from at least one of said peripheral walls substantially parallel to said top surface and said bottom surface and medially between said top and bottom surfaces; and b) said hinge is formed integral with said flanges.

4. A universal diagnostic specimen sample tray as in claim 3 wherein:

a) said hinge is a folded or rolled hinge.

5. A universal diagnostic specimen sample tray as in claim 4 wherein:

a) at least one other peripheral wall of each of said lid and said base includes a flange member having a gripping area to permit grasping for opening of said tray after closure.

6. A universal diagnostic specimen sample tray as in claim 5 wherein:

a) said gripping area includes surface texture to provide a better grasp for manual opening.

7. A universal diagnostic specimen sample tray as in claim 3 wherein:

a) said ribs include at least one pair of off-set ribs to provide, in cooperation, at least one recess for receiving a microscope slide.

8. A universal diagnostic specimen sample tray as in claim 3 wherein:

a) said primary container retaining recesses hold said containers medially of the ends of said containers, so that a variety of lengths of said containers having differently dimensioned closure members can be held in place.

9. A universal diagnostic specimen sample tray as in claim 3 wherein:

a) said tray plastic is a thermoplastic material.

10. A universal diagnostic specimen sample tray as in claim 9 wherein:

a) said thermoplastic material comprises a polymer selected from the group consisting of rigid PVC, semi-rigid PVC, polycarbonate, acrylic, impact-modified acrylic, polystyrene, impact-modified polystyrene, ABS, polyethylene, polypropylene, and combinations thereof.

11. A universal diagnostic specimen sample tray as in claim 10 wherein:

a) said thermoplastic material is biodegradable.

12. A universal diagnostic specimen sample tray as in claim 10 wherein:

a) said polymer is semi-rigid PVC.

13. A combination shippable diagnostic sample tray and tray shipping package assembly providing safe containment during shipping of a secondary diagnostic specimen sample tray having a plurality of retaining recesses for receivingly engaging a plurality of primary diagnostic sample containers for specimens having etiologic agents, comprising in operative combination:

a) a universal diagnostic specimen sample tray as in claim 1 dimensioned to be completely enclosed and sealed in a multi-layer pouch;

b) a multi-layer tray-receiving pouch having generally parallel spaced interior and exterior walls defining a central volume for receiving therein said secondary diagnostic specimen sample tray;

c) said multi-layer pouch including as said interior wall a first, interior layer contactable by said container;

d) said interior layer is easily permeable throughout its entire interior extent by liquid escaping from said primary, etiologic-agent carrying container;

e) said multi-layer pouch including as said exterior wall a second, exterior plastic layer having an external surface in contact with the external ambient environment;

f) said exterior layer is impermeable by said liquid and by hazardous vapors or etiologic agents escaping from said primary container;

g) a seal flap formed from an extension of one exterior wall layer beyond a terminal edge of an opposed exterior wall layer to define an opening to said central volume, said flap upon closure completely surrounding and isolating said secondary tray;

h) means for completely adhesively sealing said package opening in said area of flap overlap so that said seal is essentially impermeable by said hazardous liquid, or the vapors or an etiologic agent from said primary container;

i) a third layer of absorbent material disposed secured in place between said first interior layer and said second exterior plastic layer;

j) said absorbent material extending throughout the entire area of said interior layer which defines said central volume, so that upon closure of said flap, said absorbent material substantially completely encloses said secondary tray, and upon any accidental release of hazardous liquid from said tray during shipping there is absorbent material disposed immediately adjacent to any point of leakage through said permeable interior layer;
k) the density of said absorbent material layer being sufficient to contain broken shards from said primary container; and
l) the volume of said absorbent material layer being sufficient to contain and completely absorb all liquid from said primary container upon release therefrom while said exterior layer prevents leakage of liquid, vapors or etiologic agents to the external ambient environment.

14. A universal tray and shipping package assembly as in claim 13 wherein:
a) said means for completely adhesively sealing said package comprises a strip of adhesive having a release tape thereover, said adhesive strip being disposed to seal said flap to said opposed wall to form a complete seal so that said package is non-reusable and tampering with said seal is evident.

15. A universal tray and shipping package assembly as in claim 14 wherein:
a) said interior permeable layer comprises a fibrous, woven or non-woven material which retains said absorbent layer in place and permits passage of liquid therethrough for absorption by said layer;
b) said absorbent layer is cellulosic wadding;
c) said absorbent layer wadding density is above about 0.3 g/square inch; and
d) said exterior impermeable plastic layer has a thickness of greater than about 0.5 mm.

16. A universal tray and shipping package assembly as in claim 15 wherein:
a) said wadding density is in the range of from about 0.3 to about 1.0 g/square inch, and said second exterior plastic layer has a thickness in the range of from about 0.5 to about 2.5 mm.

17. A universal tray and shipping package assembly as in claim 13 wherein said third absorbent layer is cellulosic wadding.

18. A universal tray and shipping package assembly as in claim 17 wherein:
a) said interior permeable layer comprises a fibrous, woven or non-woven material which retains said absorbent wadding layer in place and permits passage of liquid therethrough for absorption by said wadding.

19. A universal tray and shipping package assembly as in claim 13 wherein:
a) said lid and said base portions include a common hinge member along one common edge to form a one-piece tray assembly in which said lid sidewalls matingly engage said base sidewalls in the closed position.

20. A universal tray and shipping package assembly as in claim 19 wherein:
a) each of said lid and said base include at least one plastic flange extending outwardly from at least one of said peripheral walls substantially parallel to said top surface and said bottom surface and medially between said top and bottom surfaces; and
b) said hinge is formed integral with said flanges.

21. A univeral tray and shipping package assembly as in claim 20 wherein:
a) said hinge is a folded or rolled hinge.

22. A universal tray and shipping package assembly as in claim 21 wherein:
a) at least one other peripheral wall of each of said lid and said base includes a flange member having a gripping area to permit grasping for opening of said tray after closure.

23. A universal tray and shipping package assembly as in claim 13 wherein:
a) said interior permeable layer comprises a fibrous, woven or non-woven material which retains said absorbent layer in place and permits passage of liquid therethrough for absorption by said layer;
b) said absorbent layer is cellulosic wadding;
c) said absorbent layer wadding density is above about 0.3 g/square inch; and
d) said exterior impermeable plastic layer has a thickness of greater than about 0.5 mm.

24. A universal tray and shipping package assembly as in claim 23 wherein:
a) said wadding density is in the range of from about 0.3 to about 1.0 g/square inch, and said second exterior plastic layer has a thickness in the range of from about 0.5 to about 2.5 mm.

* * * * *